United States Patent [19]

Parry

[11] 4,080,326
[45] Mar. 21, 1978

[54] ACETIC ACID DERIVATIVES AND PROCESSES FOR THEIR PRODUCTION

[75] Inventor: David Rees Parry, Wokingham, England

[73] Assignee: Imperial Chemical Industries Limited, London, England

[21] Appl. No.: 614,664

[22] Filed: Sep. 18, 1975

Related U.S. Application Data

[62] Division of Ser. No. 428,315, Dec. 26, 1973, Pat. No. 3,929,789.

[30] Foreign Application Priority Data

Jan. 8, 1973 United Kingdom ............... 964/73

[51] Int. Cl.² ........................................... C07D 239/36
[52] U.S. Cl. ......................... 260/256.5 R; 260/251 P; 260/251 R; 260/256.4 E; 260/256.4 C
[58] Field of Search ................. 260/256.4 C, 256.4 E, 260/256.5 R

[56] References Cited

U.S. PATENT DOCUMENTS 3,287,453 11/1966 McHattie ...................... 260/256.4 E

OTHER PUBLICATIONS

Brown et al., *Heterocyclic Compounds; The Pyrimidines*, Supplement I, 1970, Interscience, N.Y., pp. 299–300.

*Primary Examiner*—Donald G. Daus
*Assistant Examiner*—James H. Turnipseed
*Attorney, Agent, or Firm*—Cushman, Darby & Cushman

[57] ABSTRACT

A process for the preparation of a compound of formula:

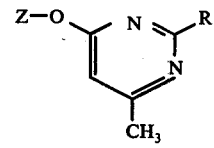

wherein R is an amino, hydrocarbylamino or dihydrocarbylamino radical, the hydrocarbylamino and dihydrocarbylamino radicals being unsubstituted, or substituted in the hydrocarbyl moiety with atoms or radicals which do not interfere with the process and Z is an acyl radical which comprises the steps of:
(a) decarboxylating a compound of formula:

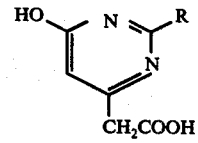

to produce the corresponding 4-hydroxy-6-methylpyrimidine; and
(b) treating the corresponding 4-hydroxy-6-methyl pyrimidine thus produced with an acylating agent capable of providing the acyl radical Z;

where both steps (a) and (b) are carried out in the same solvent or diluent.

6 Claims, No Drawings

ACETIC ACID DERIVATIVES AND PROCESSES FOR THEIR PRODUCTION

This is a division of application Ser. No. 428,315, filed Dec. 26, 1973 and now U.S. Pat. No. 3,929,789.

This invention relates to a process for preparing pyrimidine derivatives.

Accordingly the present invention provides a process for preparing a pyrimidine derivative of the formula:

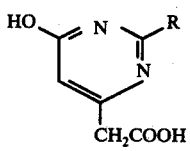

which comprises treating a guanidine of formula:

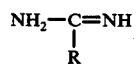

or a salt thereof, with citric acid in a strongly acid medium, wherein R is an amino, hydrocarbylamino or dihydrocarbylamino radical, said hydrocarbylamino and dihydrocarbylamino radicals being unsubstituted, or substituted in the hydrocarbyl moiety with atoms or radicals which do not interfere with the process.

Preferred strongly acidic media in which the above invention process may be performed include concentrated sulphuric acid and oleum.

As especially preferred acidic medium is 15% oleum. This is particularly effective when used at a rate of about 300–500 ml per g. mole of citric acid.

Preferably the process employs a slight molar excess (up to 20%) of citric acid with respect to the guanidine. The reaction may be carried out within a temperature range of 60°–100° C, and preferably within a range of 65°–80° C. The time taken to complete the reaction depends upon the relative quantities of the reactants, but a period of from one to four hours is generally sufficient.

Compounds which may be prepared by the above invention process include the following:
4-hydroxy-2-aminopyrimidin-6-yl acetic acid
4-hydroxy-2-ethylaminopyrimidin-6-yl acetic acid
4-hydroxy-2-dimethylaminopyrimidin-6-yl acetic acid
4-hydroxy-2-dimethylaminopyrimidin-6-yl acetic acid In a further feature the invention provides compounds of formula:

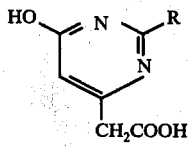

wherein R has any of the meanings given hereinabove whenever prepared by the above invention process.

In yet another feature the invention provides new compounds of the formula:

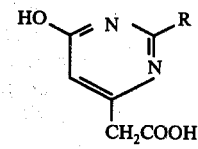

wherein R is a hydrocarbylamino or dihydrocarbylamino radical. Preferred hydrocarbylamino radicals are alkylamino radicals and preferred dihydrocarbylamino radicals are dialkylamino radicals.

The invention particularly provides the following novel compounds. 4-Hydroxy-2-ethylaminopyrimidine-6-yl acetic acid, having the formula:

4-Hydroxy-2-diethylaminopyrimidin-6-yl acetic acid, having the formula:

4-Hydroxy-2-dimethylaminopyrimidin-6-yl acetic acid, having the formula:

The compounds of formula:

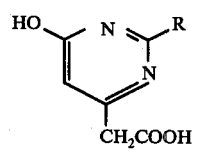

wherein R has any of the meanings given hereinbefore are useful as intermediates in the production of pesticides.

In particular 4-hydroxy-2-ethylaminopyrimidin-6-yl acetic acid may be used in the production of O,O-diethyl O (2-N-ethylacetamido)-4-methylpyrimidin 6-yl phosphorothionate, and 4-hydroxy-2-diethylaminopyrimidin-6-yl acetic acid may be used in the production of O,O-dimethyl and O,O-diethyl O(2-diethylamino-4-methylpyrimidin-6-yl) phosphorothionate.

The compounds of formula:

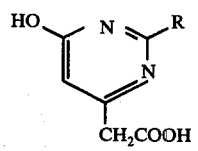

may be converted to the corresponding 4-hydroxy-6-methylpyrimidines by decarboxylation. This may be achieved by heating the compound to its melting (decomposition) point or by heating in a suitable solvent, for example, water, lower aliphatic alcohols, such as ethanol or butanol, lower aliphatic ketones such as methyl iso-butyl ketone, optionally in the presence of a base, for example an alkali metal carbonate or bicarbonate.

The decarboxylation is preferably carried out at the reflux point of the solvent, and the time required to achieve decarboxylation is generally within a period from 1 to 20 hours. When water alone is used the time required is generally more than 10 hours, but when an organic solvent is present the decarboxylation occurs much more rapidly and is generally complete in less than 10 hours.

The 4-hydroxy-6-methyl pyrimidines thus produced may subsequently be acylated, for example with a phosphoryl halide, to produce pesticidal products.

In a preferred process both the decarboxylation and acylation steps are carried out in the same solvent and reaction vessel.

In a further aspect, therefore, the invention provides a process for the preparation of a compound of formula:

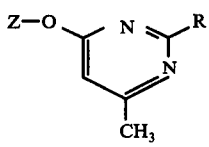

wherein R is as defined hereinabove and Z is an acyl radical which comprises the steps of:
(1) decarboxylating a compound of formula:

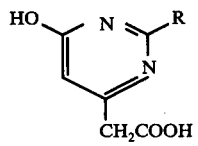

to produce the corresponding 4-hydroxy-6-methylpyrimidine; and
(2) treating the said corresponding 4-hydroxy-6-methyl pyrimidine thus produced with an acylating agent capable of providing the acyl radical Z; where both steps (1) and (2) are carried out in the same solvent or diluent, optionally in the presence of a base.

In the process defined immediately hereinabove an acylating agent includes, for example, a carboxylic acid anhydride, such as acetic anhydride, a carboxylic acid halide such as benzoyl chloride, a sulphur containing organic acid halide such as methane sulphonyl chloride and dimethylsulphamoyl chloride, a carbamic acid halide such as dimethylcarbamoyl chloride, an isothiocyanate such as methyl isothiocyanate, a phosphorus containing acid halide such as dimethylphosphorothionochloridate or diethylphosphorothionochloridate or O,N-dimethylphosphoramidochloridate or dimethylphosphonothionochloridate.

Preferably the solvent or diluent used in this process is a non-reacting one, and preferred solvents are ketones such as methyl isobutyl ketone and acetone, or halogenated compounds such as carbon tetrachloride and chloroform. Where a base is present in the process it may be used in catalytic or molar proportions. A particularly useful base is an alkali metal carbonate.

In a preferred aspect the invention provides a process for the preparation of a compound of formula:

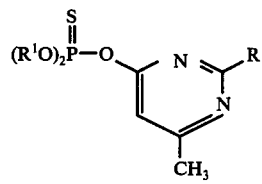

wherein R has any of the meanings given hereinbefore, and $R^1$ is methyl or ethyl, which comprises the steps of:
(1) suspending or dissolving a compound of formula:

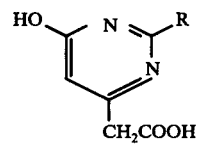

in a suitable solvent or diluent and heating the mixture so obtained, optionally in the presence of a base, to effect decarboxylation of the compound; and
(2) thereafter treating the mixture with a compound of formula:

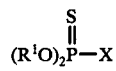

wherein X is halogen, optionally in the presence of a base.

The invention is illustrated but not limited by the following examples.

NOTE: The mixture of citric acid and concentrated sulphuric acid used in some of the preparations described in the following examples is known to evolve carbon monoxide and the preparations were therefore conducted in a fume cupboard.

EXAMPLE 1

This Example illustrates the preparation of 4-hydroxy-2-diethylaminopyrimidin-6-yl acetic acid.

Powdered citric acid monohydrate (42.0 g) was added in small portions over one hour to concentrated sulphuric acid (180 ml) at 0° C and the mixture stirred until a clear solution was obtained. N,N-Diethylguanidine sulphate (32.8 g) was added over 15 minutes and the solution stirred for one hour at the ambient temperature (ca 22°–24° C) and then at 90° C for a further 2 hours. After dilution of the mixture with deionised water (1050 ml), ammonia solution (s.g. 0.880) was added to adjust the pH to 4, and the mixture cooled to 0° C for one hour. The precipitate was collected by filtration, washed with ice-water (20 ml), acetone (100 ml), and with ether (100 ml) to yield 4-hydroxy-2-diethylaminopyrimidin-6-yl acetic acid as a white powder, having a melting point (with decomposition) of 156°–157° C.

EXAMPLE 2

This Example illustrates the conversion of the product of Example 1 to 4-hydroxy-2-diethylamino-6-methylpyrimidine.

4-Hydroxy-2-diethylaminopyrimidin-6-yl acetic acid (4.0 g) was suspended in ethanol (50 ml) and the mixture refluxed for 16 hours. The volatile portion of the mixture was then evaporated under reduced pressure to yield 4-hydroxy-2-diethylamino-6-methyl pyrimidine as a white powder, melting at 135° C.

EXAMPLE 3

This Example illustrates the preparation of 4-hydroxy-2-diethylamino-6-methylpyrimidine from citric acid without isolation of the intermediate pyrimidine acetic acid.

Powdered citric acid monohydrate (21.0 g) was added in small portions to stirred concentrated sulphuric acid (50 ml) whilst the mixture temperature was maintained at 0° C by external cooling over a period of 45 minutes. The mixture was then stirred for a further 30 minutes until a clear solution was obtained, after which diethylguanidine sulphate (16.4 g) was added over 15 minutes, and the mixture was allowed to warm to the ambient temperature over a period of one hour. The mixture was then heated at 80°-90° C for 2 hours, during which time evolution of a gas was noted. The mixture was then cooled, diluted with deionised water (300 ml) and the pH adjusted to 4 with aqueous ammonia solution (s.g. 0.880). The resultant slurry was refluxed for 3.5 hours, during which the solid precipitate slowly dissolved. The mixture was then cooled and the precipitate which was deposited collected by filtration. The aqueous filtrate was extracted with chloroform (3 × 100 ml). The material which had been collected by filtration was dissolved in the minimum quantity of cold chloroform and this solution was combined with the chloroform extract. The combined chloroform solution was washed with 10% w/v aqueous sodium bicarbonate solution, and with water, dried over anhydrous sodium sulphate and evaporated under reduced pressure to yield chromatographically pure 4-hydroxy-2-diethylamino-6-methylpyrimidine, melting at 135° C.

EXAMPLE 4

This Example illustrates the preparation of 4-hydroxy-2-ethylaminopyrimidin-6-yl acetic acid.

Using a procedure similar to that illustrated in Example 1 above, citric acid monohydrate (21.0 g) was reacted with monoethylguanidine sulphate (13.6 g) in concentrated sulphuric acid (60ml). 4-Hydroxy-2-ethylaminopyrimidin-6-yl acetic acid was precipitated from the diluted mixture by adjusting the pH to 3.5 with concentrated aqueous ammonia solution (s.g. 0.880), and collected by filtration. It melted with decomposition at 169°-170° C.

EXAMPLE 5

This Example illustrates the conversion of the product of Example 4 into 4-hydroxy-2-ethylamino-6-methylpyrimidine.

4-Hydroxy-2-ethylaminopyrimidin-6-yl acetic acid was suspended in ethanol (50 ml) and the mixture refluxed for 16 hours. Evaporation of the ethanol under reduced pressure yielded chromatographically pure 4-hydroxy-2-ethylamino-6-methylpyrimidine, melting at 176° C.

EXAMPLE 6

This Example illustrates the preparation of 4-hydroxy-2-diethylamino-6-methylpyrimidine.

A mixture of citric acid monohydrate (126.0 g) and diethylguanidine sulphate (82.0 g) was added to 15% oleum (250 ml), keeping the temperature below 30° C by external cooling. After stirring at the ambient temperature for 15 minutes to complete solubilisation the solution was heated at 70° C for 80 minutes, cooled by external cooling to 0° C, and carefully diluted with water (350 ml) and with ammonia solution (s.g. 0.880, 600 ml). The resulting slurry was heated to reflux, methyl isobutyl ketone (10 ml) being added to prevent excessive frothing. Refluxing was continued for 16 hours, after which the mixture was cooled to 70°-80° C and methyl isobutyl ketone (600 ml) added to dissolve the precipitate. The ketonic phase was separated, washed with water (2 × 100 ml) whilst still hot, and then cooled and dried over anhydrous magnesium sulphate. Evaporation of the solvent yielded chromatographically pure 4-hydroxy-2-diethylamino-6-methylpyrimidine, melting point 133°-135° C.

EXAMPLE 7

This Example illustrates the preparation of O,O-diethyl-O-2-diethylamino-6-methylpyrimidin-4-yl phosphorothionate.

A mixture of citric acid monohydrate (23.1 g) and diethylguanidine sulphate (16.4 g) was added quickly to 15% oleum (40 ml) causing the temperature to rise to 60° C. The mixture was then heated at 70° C for 90 minutes after which the solution was cooled to 50° C and diluted with water (40 ml) which caused the temperature to rise to 100° C, and the mixture was maintained at this temperature whilst ammonia solution (s.g. 0.880) was added to bring the pH to 7. Methyl isobutyl ketone (5.0 ml) was added to the slurry thus produced and the solution was heated to reflux for 15 minutes after which a further quantity of methyl isobutyl ketone (95 ml) was added and the refluxing continued for 75 minutes. The mixture was cooled to 80° C, the aqueous phase removed and the ketonic phase washed with water (25 ml). The last traces of water were then removed by azeotropic distillation after which diethylphosphorochloridothionate (17.0 g) and anhydrous potassium carbonate (18.6 g) were added to the ketonic solution and the mixture stirred at 60° C for 3 hours. The solid precipitate was removed by filtration, the filtrate washed with aqueous sodium hydroxide (2N, 75 ml), water (75 ml), dilute sulphuric acid (2N, 75 ml) and finally water (2 × 75 ml). The ketonic phase was dried over anhydrous magnesium sulphate, and the solvent removed by evaporation under reduced pressure to yield O,O-diethyl O-2-diethylamino-6-methylpyrimidin-4-yl phosphorothionate as a pale yellow oil, spectroscopically and chromatographically identical with an authentic sample.

I claim:

1. A process for the preparation of a compound of formula:

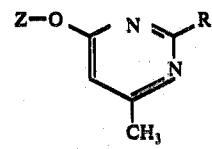

wherein R is amino, ethylamino, diemthylamino or diethylamino and Z is an acyl radical selected from the group consisting of acetyl, benzoyl, methane sulphonyl, dimethylsulphamoyl, dimethylcarbamoyl, methylthiocarbamoyl, dimethylphosphorothionyl, diethylphosphorothionyl, O,N-dimethylphosphoroamidoyl and dimethylphosphorothionyl which comprises the steps of:

(a) decarboxylating a compound of formula:

in the presence of a base selected from the group consisting of alkali metal carbonates and bicarbonates, to produce the corresponding 4-hydroxy-6-methylpyrimidine; and (b) treating the said corresponding 4-hydroxy-6-methyl pyrimidine thus produced with an acylating agent selected from the group consisting of acetic anhydride, benzoyl chloride, methane sulphonyl chloride, dimethylsulphamoyl chloride, dimethylcarbamoyl chloride, methyl isothiocyanate, dimethylphosphorothionochloridate, diethylphosphorochloridothionate, O,N-dimethyl-phosphoramidochloridate and dimethylphosphonochloridothionate;

where both steps (a) and (b) are carried out in the same solvent or diluent.

2. A process as claimed in claim 1 wherein the base is an alkali metal carbonate.

3. A process as claimed in claim 1 wherein the solvent or diluent is a ketone.

4. A process as claimed in claim 3 wherein the solvent or diluent is methyl isobutyl ketone.

5. A process as claimed in claim 1 wherein the solvent is carbon tetrachloride or chloroform.

6. A process for the preparation of a compound of formula:

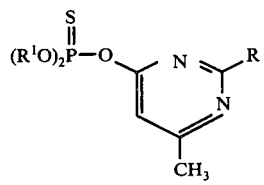

wherein R is amino, ethylamino, dimethylamino or diethylamino and $R^1$ is methyl or ethyl, which comprises the steps of:

(a) suspending or dissolving a compound of formula:

in a solvent or diluent and heating the mixture so obtained in the presence of a base selected from the group consisting of alkali metal carbonates and bicarbonates to effect decarboxylation of the compound, and (b) thereafter treating the mixture with a compound of formula:

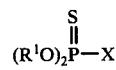

where X is halogen.

* * * * *